United States Patent
Uddin

(10) Patent No.: US 10,493,050 B2
(45) Date of Patent: Dec. 3, 2019

(54) BROAD SPECTRUM PHARMACOLOGICAL COMPOSITION FOR TREATMENTOF VARIOUS INFECTIONS AND DISEASES AND METHODSOF USE

(71) Applicant: Naeem Uddin, Karachi (PK)

(72) Inventor: Naeem Uddin, Karachi (PK)

( * ) Notice: Subject to any disclaimer, the term of this patent is extended or adjusted under 35 U.S.C. 154(b) by 102 days.

(21) Appl. No.: 15/891,839

(22) Filed: Feb. 8, 2018

(65) Prior Publication Data

US 2018/0161294 A1     Jun. 14, 2018

Related U.S. Application Data

(63) Continuation-in-part of application No. 15/062,156, filed on Mar. 6, 2016, now Pat. No. 9,962,347, which is a continuation-in-part of application No. 13/913,555, filed on Jun. 10, 2013, now Pat. No. 9,301,935.

(51) Int. Cl.
    *A61K 31/194*     (2006.01)
    *A61P 43/00*     (2006.01)
    *A61K 9/00*     (2006.01)

(52) U.S. Cl.
CPC .......... *A61K 31/194* (2013.01); *A61K 9/0012* (2013.01); *A61P 43/00* (2018.01); *A61K 2300/00* (2013.01)

(58) Field of Classification Search
CPC ...... A61K 31/194; A61K 31/573; A61K 9/14; A61K 9/107; A61K 9/0095; A61K 9/08
See application file for complete search history.

(56) References Cited

U.S. PATENT DOCUMENTS

| | | |
|---|---|---|
| 5,639,459 A | 6/1997 | Bouras |
| 5,648,389 A | 7/1997 | Gans et al. |
| 6,407,141 B1 * | 6/2002 | Hart .................... A61K 31/194 514/574 |
| 6,936,579 B2 | 8/2005 | Urban |
| 6,982,097 B2 | 1/2006 | Mingzhong et al. |
| 7,517,842 B2 | 4/2009 | Barnhart et al. |
| 7,618,658 B2 | 11/2009 | Tsuchida et al. |
| 7,883,715 B2 | 2/2011 | Abraham et al. |
| 2007/0027119 A1 | 2/2007 | Ahmed et al. |
| 2007/0184016 A1 | 8/2007 | Macinga et al. |
| 2010/0234460 A1 | 9/2010 | Foret et al. |
| 2010/0292333 A1 | 11/2010 | Mladenovich |
| 2011/0152384 A1 | 6/2011 | Gunn et al. |
| 2012/0015809 A1 | 1/2012 | He et al. |
| 2012/0269751 A1 | 10/2012 | Stal |
| 2012/0302642 A1 | 11/2012 | Post |

OTHER PUBLICATIONS

Sigmundsdottir, Trends in Pharmacological Sciences 31 (2010) 239-245.

R Von Burg, Journal of Applied Toxicology, vol. 14(3),233-237 (1994).

* cited by examiner

*Primary Examiner* — Angela C Brown-Pettigrew
(74) *Attorney, Agent, or Firm* — Michael E. Zall

(57) ABSTRACT

A pharmacological composition for the treatment of bacterial and protozoal infections in a patient. The preferred pharmacological composition comprises a pharmaceutical carrier and an active composition selected from the group consisting of: a) an amount of sodium oxalate and an amount of oxalic acid, b) an amount of sodium citrate and an amount of citric acid, or c) mixtures of a) and b). The amounts and weight ratios of a) the sodium oxalate and oxalic acid, and b) the sodium citrate and citric acid in the active composition are such as to produce a safe and effective pharmacological composition. Sodium salts of other carboxylic acids may be used. The invention also relates to the method of using the pharmacological composition for the safe and effective treatment of bacterial infections, protozoal infections and dermatological diseases.

7 Claims, No Drawings

BROAD SPECTRUM PHARMACOLOGICAL COMPOSITION FOR TREATMENT OF VARIOUS INFECTIONS AND DISEASES AND METHODS OF USE

RELATED APPLICATIONS

This application is a continuation in part of U.S. application Ser. No. 15/062,156 filed on Mar. 6, 2016, now U.S. Pat. No. 9,962,347, issued on May 8, 2018, which is a continuation in part of U.S. application Ser. No. 13/913,555 filed on Jun. 10, 2013, now U.S. Pat. No. 9,301,935 B2 issued on Apr. 5, 2016, the entire disclosures of which are incorporated herein by reference.

BACKGROUND OF THE INVENTION

Field of the Invention

The present invention relates to a pharmacological composition that is a safe and effective broad spectrum antibiotic, particularly against gram positive and gram negative bacteria, anti-protozoal, and can be used for the treatment of various diseases and for the treatment of various dermatological disorders in patients. In particular, the composition of this invention, inhibits the growth or destroys the bacteria, and inhibits or destroys protozoal infections. In particular the composition of this invention ameliorates, prevents and/or treats bacterial infectious diseases. The active ingredients in the preferred pharmacological composition are a) a mixture of sodium citrate and citric acid, and/or b) a mixture of sodium oxalate and oxalic acid. However, similar mixtures of the active cation of sodium salts with anions of organic acids may be derived from other organic acids other than citric and oxalic acids, for example, lactic acid, salicylic acid, tartaric acid, glycolic acid, ascorbic acid, maleic acid, succinic acid, mandelic acid, dodecylbenzenesulfonic acid, propionic acid, gluconic acid, malic acid, benzoic acid, aspartic acid, acetic acid, glutamic acid, adipic acid, hexanoic acid, octanoic acid, nonanoic acid, decanoic acid, undecanoic acid and combinations thereof. The compositions of this invention may be administered orally.

Related Art

Applicant is aware of the following references that may be relevant to this invention:
US Published Application 2007/0027119 to Ahmed et al. describes a nonirritating antimicrobial liquid composition with citric acid and oxalic acid combination and alcohol used in skin treatment, primarily a teat treatment for cows.
US Published Application 2007/0184016 to Macinga et al. describes a pre-surgical disinfectant with alcohol and citric acid, oxalic acid or mixtures thereof.
US Published Application 2010/0234460 to Foret et al. describes disinfectant solution for the treatment of hoof diseases that contains a surfactant and one or more carboxylic acids, e.g., citric acid and oxalic acid.
US Published Application 2010/0292333 to Mladenovich describes fungal infection treatment composed of two or more low-molecular weight organic acids, e.g., oxalic acid and citric acid, and their salts.
US Published Application 2011/0152384 to Gunn et al. describes skin care composition with emulsifier and organic acids, including oxalic acid or citric acid.
US Published Application 2012/0015809 to He et al. describes a surface cleaner with formic acid and an enhancing component of citric acid that may be mixed with oxalic acid for the control of pests, including fungi, oomycetes, nematodes and weeds.
US Published Application 2012/0269751 to Stal describes a topical composition of physiologically acceptable carboxylic acid such as citric acid and/or oxalic acid for the treatment of skin and nail conditions, i.e., microbiological infections of the nail (onychomycosis), warts.
US Published Application 2012/0302642 to Post abrasive acidic cleaning composition for hard surfaces, e.g., lavatory surfaces, which includes a colloid forming clay, a thickener, a surfactant and antimicrobial amounts of an organic acid and an abrasive constituent. The organic acid may be a citric acid, oxalic acid or mixtures thereof.
U.S. Pat. No. 5,639,459 to Bouras describes a composition to treat hair loss, baldness and alopecia that embodies using oxalates, e.g., ammonium oxalate meta. The use of citric acid is in conjunction therewith is taught. The treatment " . . . enhances the aesthetic appearance of scalp and skin."
U.S. Pat. No. 5,648,389 to Gans et al. describes a topical treatment for dermatological disorders using zinc compound and a hydroxy acid that may be citric acid and the zinc compound may be zinc oxalate.
U.S. Pat. No. 6,936,579 to Urban describes a hard surface cleaning composition with citric acid and oxalic acid.
U.S. Pat. No. 6,982,097 to Mingzhong et al. describes a biocide composition for disinfecting water that includes a filler of sodium citrate, oxalic acid, sodium bromide, and a halogen releasing compound.
U.S. Pat. No. 7,517,842 to Barnhart et al. describes an antimicrobial hand wash formulation with a cationic surfactant produced from the neutralization of an amidoamine with an acid and an active ingredient. The acid may be an oxalic acid or citric acid as the acid neutralizer.
U.S. Pat. No. 7,618,658 to Tsuchida et al. describes an antimicrobial composition of Sasaextract and the use of citric acid or oxalic acid to improve the antimicrobial activity.
U.S. Pat. No. 7,883,715 to Abraham et al. describes enhancing the herbicidal effectiveness of glyphosate through the addition of a dicarboxylic acid, in particular oxalic acid.
U.S. Pat. No. 6,407,141 to Hart describes hemo-therapeutic chemo-preventative composition for treating vascular diseases that contains oxalic acid and/or oxalate.
Citric Acid Citric acid is well known. Citric acid was first isolated in 1784 by the chemist Wilhelm Scheele, who crystallized it from lemon juice. Industrial-scale citric acid production first began in 1890. In 1893, C. Wehmer discovered penicillium mold could produce citric acid. In 1917, American food chemist James Currie discovered certain strains of the mold *Aspergillus niger* could be efficient citric acid producer.

Citric Acid, 2-hydroxytricarboxylic acid is of biological origin and its functionality makes it suitable for wide range of application. The presence of one hydroxyl group and 3 carboxyl groups permits the formation of complex molecules, which may be soluble and capable of modifying the solubility of constituent's material. Citric acids, Oxalic acid, along with lactic acid, acidulant and its salts are preferred buffers in pharmaceutical preparation. Citric acid crystallizes from a cold aqueous solution as monohydrate (C6H8O7H2O). The crystal is color less. It is optically inactive. Citric acid is strong organic acid as indicated by the first dissociation constant which is $8.2 \times 10^{-4}$ at 18 degree Celsius. The second and third dissociation constants are $1.77 \times 10^{-4}$ and $3.9 \times 10^{-7}$ respectively. Citric acid is readily soluble in water and in various organic compounds.

Citric acid is a natural preservative present in citrus fruits. It is white hygroscopic crystalline powder. It can exist either in an anhydrous (water-free) form or as monohydrate. Citric acid also dissolves in absolute (anhydrous) ethanol. It is also used to add an acidic or sour taste to foods and drinks and is used mainly as acidifier, flavoring and chelating agent.

The FDA lists citric acid in the Nov. 20, 1959 issue of the federal register (23-a) as a substance that is generally recognized as safe for specific use in compliance with the Food additive amendment of 1958. Even at high concentrations citric acid is not injurious in contact with skin.

After oral administration of citric acid the citrate ion is rapidly and almost completely oxidized, less than 1% being excreted unchanged in urine. Intravenous injection shortens, coagulation times of the blood but in vitro, the citrate ion acts as an anticoagulant.

With sodium bicarbonate, citric acid is used in many effervescent powder and tablets to liberate carbon dioxide when added to water. Citric acid salt's such as sodium citrate and potassium citrate and citric acid are also used in different remedies like in CITRO-SODA® (Abbott Laboratories) which is characterized as a gastric antacid and urinary alkalinizing agent.

Sodium Citrate

Sodium Citrates are used as acidity regulators in food and drinks, and also as emulsifiers for oils, e.g., with citric acid it is used as a buffering agent for controlling PH in the preparation of candies In pharmaceutical preparations, such as effervescent tablets, powders and droughts, sodium citrate is used as blood and urinary alkalizer and in large dosages as a saline cathartic. Due to its anticoagulant property of citrate ion, sodium citrate is extensively employed for this purpose. And the final product is known officially in US Pharmacopeia as citrated, normal human plasma when blood is drawn from an individual under aseptic condition into sterile bottle. Such bottle contains 50 ml of a 4% solution of sodium citrate in isotonic sodium chloride solution. To this is added 50 ml of whole blood. Sodium Citrate prevents blood from coagulation.

OBJECTS AND SUMMARY OF THE INVENTION

The present invention is directed to a pharmacological composition for the treatment of bacterial and protozoal infections in a patient. The pharmacological composition comprises a pharmaceutical carrier and an active composition selected from the group consisting of an amount of an active cation sodium salt with an anion organic acid and an amount of the organic. The organic acid is selected from the group consisting of citric acid, oxalic acids, lactic acid, salicylic acid, tartaric acid, glycolic acid, ascorbic acid, maleic acid, succinic acid, mandelic acid, dodecylbenzenesulfonic acid, propionic acid, gluconic acid, malic acid, benzoic acid, aspartic acid, acetic acid, glutamic acid, adipic acid, hexanoic acid, octanoic acid, nonanoic acid, decanoic acid, undecanoic acid or combinations thereof. The amounts and weight ratios of such amounts in the active composition result in a safe and effective pharmacological composition.

The preferred pharmacological composition comprises a pharmaceutical carrier and an active composition selected from the group consisting of:
a. an amount of sodium oxalate and an amount of oxalic acid,
b. an amount of sodium citrate and an amount of citric acid, or
c. mixtures of a and b, The amounts and weight ratios of a) the sodium oxalate and oxalic acid, and b) the sodium citrate and citric acid in the active composition are such as to produce a safe and effective pharmacological composition.

The invention also relates to the method of using the pharmacological composition for the safe and effective treatment of bacterial infections, protozoal infections and dermatological diseases.

DETAILED DESCRIPTION OF THE INVENTION

Unless specified otherwise, all ingredients are in weight/weight percent (w/w %), i.e., the weight of the ingredient relative to the weight of the final composition described as a percentage.

A "therapeutically effective amount" means the amount of the pharmacological composition described herein that will disinfect, inactivate or significantly diminish the population of a microorganism or protozoa, or effectively treat a given disease or condition, e.g., bacterial infection, protozoal infection, or dermatological diseases or infections.

Preferred Active Composition: Sodium Oxalate and Oxalic Acid

The theoretical stoichiometric ratio of oxalic acid and sodium bicarbonate for the preparation of sodium oxalate is 1:1.33 weight ratios. Theoretically this produces 100% sodium oxalate.

The active composition used in the pharmacological compositions of this invention uses a 1:1 weight ratio of oxalic acid to sodium bicarbonate to make the active composition. This produces a final active composition with an excess of oxalic acid mixed with sodium oxalate. This imparts a safe and efficacious medicinal activity to the composition. The active composition maintains a pH of about 6 which acceptable for patient use.

The highly preferred composition is a mixture of 78.44% sodium oxalate and 21.56% oxalic acid. A preferred range is about 73% to about 83% Sodium oxalate and about 17% to about 27% oxalic acid. It is to be understood however that various weights and ratios of sodium oxalate and oxalic acid may be used as long as a safe and efficacious pharmacological composition is produced.

Sodium Oxalate-Oxalic Acid Mixture a) Stoichiometric Formulation Ratio:

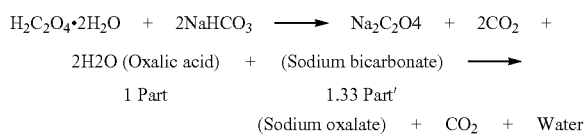

b) Method of Producing Active Composition:

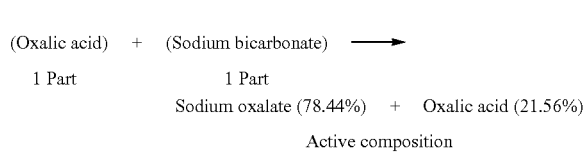

Method of Preparation of Mixture of Sodium Oxalate-Oxalic Acid as Active Ingredient Mix one part oxalic acid and one part sodium bicarbonate than gradually spray sterile water into the mixture to make reaction. The water is merely the medium for the reaction. Carbon dioxide is evaporated rapidly and water is gradually evaporated. The remaining product is a mixture of 78.44% Sodium Oxalate and 21.56% Oxalic acid active ingredient. The product is in the form of crystals. The product is then dried and crushed to fine particles to produce an active composition suitable for formulation into the pharmacological formulations of this invention.

Preferred Active Composition: Sodium Citrate and Citric Acid

The theoretical stoichiometric ratio of citric acid and sodium bicarbonate for the preparation of sodium oxalate is 1:1.2 weight ratios. Theoretically this produces 100% sodium citrate. The active composition used in the pharmacological compositions of this invention uses a 1:1 weight ratio of citric acid to sodium bicarbonate to make the active composition. This produces a final active composition with an excess of citric acid mixed with sodium citrate. This imparts a safe and efficacious medicinal activity to the composition. The active composition maintains a pH of about 6 which acceptable for patient use.

The highly preferred composition is a mixture of 87% sodium citrate and 13% citric acid. A preferred range is about 82% to about 92% Sodium citrate and about 8% to about 18% citric acid. It is to be understood however that various weights and ratios of sodium citrate and citric acid may be used as long as a safe and efficacious pharmacological composition is produced.

Sodium Citrate-Citric Acid Mixture a) Stoichiometric Formulation ratio:

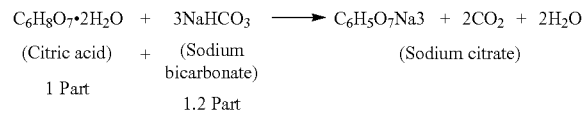

b) Method of Producing Active Composition:

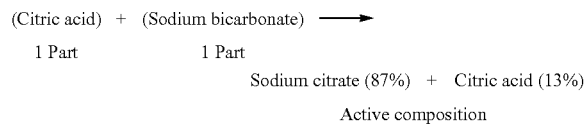

Method of Preparation of Mixture of Sodium Citrate-Citric Acid as Active Ingredient Mix one part citric acid and one part sodium bicarbonate than gradually spray sterile water into the mixture to make reaction. The water is merely the medium for the reaction. Carbon dioxide is evaporated rapidly and water is gradually evaporated. The remaining product is a mixture of 87% Sodium citrate and 13% citric acid active ingredient. The product is in the form of crystals. The product is then dried and crushed to fine particles to produce an active composition suitable for formulation into the pharmacological formulations of this invention.

Similar mixtures of sodium salts and organic acids may be derived from other organic acids other than citric and oxalic acids, for example, lactic acid, salicylic acid, tartaric acid, glycolic acid, ascorbic acid, maleic acid, succinic acid, mandelic acid, dodecylbenzenesulfonic acid, propionic acid, gluconic acid, malic acid, benzoic acid, aspartic acid, acetic acid, glutamic acid, adipic acid, hexanoic acid, octanoic acid, nonanoic acid, decanoic acid, undecanoic acid and combinations thereof.

The pharmacological compositions of this invention include a pharmaceutically acceptable carrier that does not adversely affect the efficacy and safety of the compositions. The carrier is highly dependent on the selected modality of treatment. For example, the pharmacological compositions may be orally administered, topically applied, administered as a suppository, and as an injectable. The carrier may include, for example, an additive selected from a buffering agent, an emollient, a humectant, a preservative, a surfactant or wetting agent, a viscosity control agent, a colorant, an opacifying agent, and any combinations thereof.

The pharmacological composition may also include additional suitable components, for instance fragrances, emulsifiers, detergents, antioxidants and preservatives, and other ingredients commonly used in pharmaceutical and cosmetic formulations. Preferably, the composition is essentially free of water, which increases the stability of the composition over time. Preferably, the composition is formulated as a fluid composition such as a cream, or more preferably as a liquid composition, which is relatively easy to apply to the human skin and/or nails.

Methods of preparing the pharmacological compositions may involve dissolving a desired concentration of the active composition and, alternatively, any desired additives in a selected pharmaceutical carrier. The solution is then mixed, for example in a mixer, to form a final pharmacological composition. Useful concentrations are those where the percentage of the active composition by total weight of the composition is preferably from about 0.02 to 20% by weight of the pharmacological composition. The pharmaceutical carrier may be present form 80 to 99.98% by weight. More preferably, this is from about 0.03 to 15% of each active composition and from about 85 to 99.97% of a pharmaceutical carrier.

The phrase "therapeutically effective amount" is intended to qualify the amount of the pharmacological composition which will achieve the goal of the composition, e.g., reduction of bacteria, reduction of protozoal activity, and treatment of dermatological diseases. "Therapeutically effective" may also refer to improvement in disorder severity or the frequency of incidence over no treatment.

The term "topical" and "locally" application shall refer to any composition applied on skin, eye, auditory canal, oral mucosa and in vaginal mucosa where the application of my invention is indicated.

Broadly, the pharmacological composition of this invention is used for the treatment of bacterial and protozoal infections in a patient and treating a dermatological disease in a patient.

The pharmacological compositions of this invention may also contain water and a "structuring agent" such as carbomers or other thickening polymers, for example, xanthan gum, carrageenan gum or the like. The compositions may be made into a wide variety of product types that include but are not limited to lotions, sprays, wipes, and make-up such as foundations. These product types may comprise several types of cosmetically-acceptable topical carriers. Preferably the carrier is alcohol free.

Preferred carriers for the active composition, based on the foregoing criteria for use, are:

Preferred Carrier Compositions (by Weight):
1) 20% emulsifying wax, 10% Liquid paraffin and 70% water.
2) 20% emulsifying wax and 80% water.
3) 2% carboxymethyl cellulose and 98% water.

Antibiotic

More specifically the pharmacological compositions are used as a broad spectrum antibiotic. Preferably, the mixture of sodium oxalate and oxalic acid is used alone as the active composition, as is the mixture of sodium citrate and citric acid. A mixture of these active compositions may also be used.

The pharmacological composition of this invention may be used orally, topically in the form of ointment, cream, and drops (for eye and ear) through suppository and parentally by injection, infusion or implantation. The pharmacological compositions of this invention are effective against gram positive and gram negative bacteria, for example: *Staphylococcus aureus, Epidermidis, Streptococcus Aagalactae, E. coli, Klebsilla, Proteus*, Entrobacter, Entrococcous, *Citrobacter, Propionibacterium acne, Corynebacterium, B. Subtilis*, and *Serratia* but not limited to these.

The pharmacological composition of this invention may be used where antibiotics are indicated in the treatment of infections caused by pathogens sensitive to it, for example in pneumonia, chronic bronchitis, acute exacerbation of chronic bronchitis, community acquired pneumonia, sinusitis otitis media, urinary tract infection, genital tract gonococci urethritis, non gonococci urethritis, cervicitis, skin and soft tissue infections, chalazion, conjunctivitis, otitis externa, otitis media tympanits, perotinitis, cholecystis, appendicitis, folliculitis, paronychia, carbuncle and other such infections.

Protozoa

The pharmacological compositions of this invention may be used for reducing protozoa in a patient having a protozoal infection, i.e., an anti-protozoal composition. The composition acts against trichomonads which causes trichomoniasis. It also acts against antamoeba histolytica, causes amaebiasis and Giardia, causes Giardiasis the gastroenteritis intestinalis. Some other protozoa are human parasites, causing diseases. Examples of diseases caused by protozoa, which the compositions of this invention are effective against, are Malaria, Amoebiasis, Giardiasis, Toxoplasmosis, Cryptosporidiosis, Trichomoniasis, Chagas disease, Leishmaniasis, Sleeping Sickness, and Dysentery.

Dermatological Diseases

The pharmacological compositions of this invention may be used for treating dermatological diseases in a patient having such a disease. Preferably, the mixture of sodium oxalate and oxalic acid is used alone as the active composition, as may the mixture of sodium citrate and citric acid. A preferred dermatological pharmacological composition of this invention for the treatment of skin diseases includes about 1% to about 10% of the sodium oxalate and oxalic acid mixture as the active composition or about 1% to about 10% of the sodium citrate and citric acid as the active composition. Optionally, about 1% to about 4% Salicylic acid, steroid (colobetasol, hydrocortisone), Benzoic acid and zinc oxide may be added to enhance the effect of composition. For dry skin, an oily base may be used. For an oily skin, a water base may be used. If the pharmacological composition needs to be taken orally, a nontoxic (edible) water based carrier should be used. If the pharmacological composition is for vaginal use a water or oil base carrier should be used.

Hyperhidrosis

The pharmacological compositions of this invention may also be used for treating hyperhidrosis. Hyperhidrosis is a disease of excessive production of sweat, particularly from the palms, soles and axillae. Hyperhidrosis may be due to pharmacologically acting agents acting on the sweat glands, abnormal stimulation of the sympathetic path-ways between the hypothalamus and nerve endings or over activity of one of three different centers responsible for thermoregulatory, mental and gustatory centers or of unknown cases.

Whatever the underlying cause of hyperhidrosis, the pharmacological compositions of this invention act locally to suppress and/or cure hyperhidrosis by developing anhidrotic areas by directly acting on the sweat glands (eccrine and apocrine glands).

The preferred treatment is with a topical pharmacological composition having 2% to 10% (by weight) of a mixture of sodium citrate and citric acid or, alternatively with a 2% to 10% mixture of sodium oxalate and oxalic acid.

Lice

The pharmacological compositions of this invention may also be used for treating lice. This is accomplished by the direct interference by the compositions of this invention with the respiratory function of the lice by blocking the spiracles of the lice. This is accomplished without any adverse effect on the skin, and particularly to children that would use the composition.

Lice are members of phthiraptera. They spend their entire life on the host, e.g., animals or people. Man is parasitized by two species. Two species are from the sub-order anoplura, and are the *Pediculushumanus* and *Pithrus pubis* species. There are two species of *Pediculus humanus*; they are *P humanus capitis* (head lice) and *P humanus humanus* (body or clothing lice). *Pithirus pubis* (pubic or crab lice) is morphologically quite distinct from *Pediculus humanus*. Infection with pubic lice is termed pithiriasis while infection with *Pediculus humanus* is termed Pediculosis.

The pharmacological compositions of this invention produce a multi action affect to eradicate the lice. It is pediculicider and ovicider. Eggs of head lice, and empty egg cases are cemented to hair shaft with a chitinous cement material secreted by the female accessory glands and are difficult to dislodge. The compositions of this invention dissolve chitinous material to loosen the eggs so that they can be removed by combing the hair. The pharmacological compositions also have antihydrotic effect and create anhidrotic area in scalp which creates an unfavorable environment for lice development. The compositions when applied locally will kill the lice within 24 hours.

The preferred treatment is with topical pharmacological compositions of a 2% to 10% (by weight) of a mixture of sodium citrate and citric acid or, alternatively with a 2% to 10% mixture of sodium oxalate and oxalic acid.

Scabies

The pharmacological compositions of this invention may also be used for treating Scabies. This is a disease found in man and animal. It is caused by *sarcoptes* scabie and notoedres cati. Scabies are caused by mites of Arachnida class *Sarcoptes scabiei*.

The mite shows a preference for certain sites in which to burrow and appear to avoid areas with a high density of pilosebeceous follicle. The number of adult female mites in individual suffering from the common form of scabies is about twelve. Only in crusted scabies there are a large number of mites present.

Scabies is usually transmitted by close physical contact such as prolonged hand holding, bed sharing. Poor hygienic condition, encourage the spread of scabies. Scabies is usually found in developing countries and regions of poverty.

The pharmacological compositions of this invention when locally applied are scabicider and functions to minimize secretions from the sebaceous glands. Secretions from the sebaceous glands provide a suitable environment for the growth of mites in humans as well as in animals. The compositions provide a "double action" for the treatment of this disease.

The preferred treatment is with topical pharmacological compositions of a 2% to 10% (by weight) of a mixture of sodium citrate and citric acid or, alternatively with a 2% to 10% mixture of sodium oxalate and oxalic acid. Oral treatment for scabies may also be given for short period of time orally which also work as scabicider.

Fish Malodor

The pharmacological compositions of this invention may also be used for treating Fish malodor caused by sweating, vaginal discharge and/or from mouth and nares. Trimethylaminuria (TMAU), also known as fish odor syndrome or fish malodor syndrome, is a rare metabolic disorder that causes a defect in the normal production of the enzyme flavin containing monooxygenase ("FM03"). When FMO3 is not working correctly or if not enough enzyme is produced, the body loses the ability to properly convert trimethylamine (TMA) from precursor compounds in food digestion into trimethylamine oxide (TMAO) through a process called N-oxygenation. Trimethylamine then builds up and is released in the person's sweat, urine, and breath, giving off a strong fishy odor or strong body odor. Other names: Mal fish odor smell from sweating, Bromhidrosis and fish odor syndrome and osmidrosis.

Odor of skin in men to a large extend determined by apocrine glands secretion. Sebeceous glands secretions have some odor also. Decomposition of keratinization especially in the presence of hyperhidrosis produces offensive smell. Eccrine gland secretion is odorless but various substances may be excreted in it for example garlic.

Characteristic odors may be associated with various uncommon amino-acidurias; trimethyl-aminuria gives rise to the fish odor syndrome. This odor is unpleasant and people avoid sitting near such persons.

The pharmacological compositions of this invention act as a deodorant by rendering the application area anhidrotic. As it suppresses the sweat secretion of both apocrine and eccrine sweat gland it also suppressessebecous gland secretion sebum. It also prevents bacterial activity which decomposes and liberates fatty acids with its characteristic smell. The pharmacological compositions of this invention were used by 30 patients and the composition was efficacious.

The preferred treatment is with topical pharmacological compositions of a 2% to 10% (by weight) of a mixture of sodium citrate and citric acid or, alternatively with a 2% to 10% mixture of sodium oxalate and oxalic acid.

Vaginal Mal Fish Odor

The pharmacological compositions of this invention may also be used for treating vaginal mal fish odor. This is the commonest form of vaginitis. The patient complains of an excessive grey, thin discharge associated with a fishy odor. This disorder is associated with infection by aerobic Gram negative rod known as *gardnerella* vaginitis. This organism alone is incapable of causing infection and now specific vaginitis is now regarded as complex interrelationship between *gardnerella* and anaerobic species of bacteria of which genus *mobiluncus* have been identified only and their over growth within the vagina give increase in secretion and fishy mal odor.

The preferred treatment is with topical pharmacological compositions of a 2% to 5% (by weight) of a mixture of sodium citrate and citric acid or, alternatively with a 2% to 10% mixture of sodium oxalate and oxalic acid.

Mal Fish Odor from Mouth

Mal fish odor from mouth and nose is a bad and unpleasant smell from the mouth and nose.

The preferred treatment is with a topical pharmacological composition of a 2% to 10% (by weight) of a mixture of sodium citrate and citric acid or, alternatively with a 2% to 10% mixture of sodium oxalate and oxalic acid.

Morphoea

The pharmacological compositions of this invention may also be used for treating Morphoea (Sclerosis of skin). Morphea is a medical term for localized scleroderma. The disease involves isolated patches of hardened skin—there generally is no internal organ involvement. The condition may be subdivided clinically into many types. In this disease skin become thickened, elastic tissue is reduced and the skin becomes hard. The surface is usually smooth and the wrinkles in the skin are lost. Facial expressions may also be lost.

The pharmacological compositions of this invention when topically applied cause resolution of such cases with excellent results.

The preferred treatment is with topical pharmacological compositions of a 2% to 10% (by weight) of a mixture of sodium citrate and citric acid or, alternatively with a 2% to 10% mixture of sodium oxalate and oxalic acid. From 1% to 2% salicylic acid and/or 0.025% to 0.05% clobetasol propionate may be added to the pharmacological composition.

Hypermelanosis

The pharmacological compositions of this invention may also be used for treating Hypermelanosis, a condition where there is excessive melanin deposition in the skin or in the oral mucous. This may be congenital or acquired through a drug reaction, melasma, addisions diseases, dyskeratosis congenital, post inflammatory hypermelanosis, berloque dermatitis, hypermelasnosis due to naevus of ITO, blue naevus, photodynamic and phototoxic reaction, hepatic cirrhosis (cause diffuse pigmentation), amyloidosis, pellagra, Mongolian spots and etc.

The pharmacological compositions of this invention when locally applied cures, diminishes or decreases such hypermelanotic pigmented spots.

The preferred treatment is with topical pharmacological compositions of a 2% to 10% (by weight) of a mixture of sodium citrate and citric acid or, alternatively with a 2% to 10% mixture of sodium oxalate and oxalic acid. Additionally, 0.025% to 0.05% clobetasol propionate and 2% to 3% salicylic acid may be added to the pharmacological composition.

Deformed Nails

The pharmacological compositions of this invention may also be used for treating Deformed Nails. Such nails are either congenitally or acquired through activity and environment. Without limiting the scope of the invention, there are several type nail deformities:
 1. Habit deformity—the deformity consists of a depression down the center of one nail.
 2. Splitting into layers—the tips of the nails split into layers and pieces may flake.
 3. Onychogryphosis—the nail become curved like a ram's horn.
 4. Beau's lines—a transverse depression in nails.
 5. Regular pitting—Excess ridging with or without pitting.

The preferred treatment is with topical pharmacological compositions of a 2% to 10% (by weight) of a mixture of sodium citrate and citric acid or, alternatively with a 2% to 10% mixture of sodium oxalate and oxalic acid.

Nail Growth

The pharmacological compositions of this invention may be used to enhance the growth of nails which are broken before attaining its normal length.

The preferred treatment is with topical pharmacological compositions of a 2% to 10% (by weight) of a mixture of sodium citrate and citric acid or, alternatively with a 2% to 10% mixture of sodium oxalate and oxalic acid.

Hair Fall and Alopecia

The pharmacological compositions of this invention may also be used for effectively treating Hair Fall and Alopecia.

The preferred treatment is with topical pharmacological compositions of a 2% to 5% (by weight) of a mixture of sodium citrate and citric acid or, alternatively with a 2% to 5% mixture of sodium oxalate and oxalic acid. Optionally, 1.5% salicylic acid, 3% benzoic acid and 0.025% clobetasol propionate may be added.

Rosacea.

The pharmacological compositions of this invention may also be used for treating Rosacea. Rosecea is a chronic skin disorder, usually affecting the convexities of the face and characterized by redness of the skin, telengiectasia and episodes of inflammation. During an attack of inflammation the effected skin typically develops papules, pustules and swelling. The disease is common at ages 30-50 years old. The disease is also prominent in women.

Cardinal physical signs include 1) Erythema 2) Talengiectasia 3) Papules 4) Swelling 5) Pustules. The pharmacological compositions of this invention when therapeutically and locally applied reduce inflammation, anti-erythematic and keratolytic activity and reduce the number of episodes.

The preferred treatment is with topical pharmacological compositions of a 1% to 5% (by weight) of a mixture of sodium citrate and citric acid or, alternatively with a 1% to 5% mixture of sodium oxalate and oxalic acid. Additionally, optionally 5% to 10% zinc oxide may be added as sun screening agent and also as to prevent irritation to the composition.

Acne

The pharmacological compositions of this invention may also be used for treating acne. All types of acne may be treated.

Acne is chronic inflammatory disease affecting more than 80% of adolescents and may continue through adulthood. Some individuals suffer from acne into the thirties and even beyond. Lesion acne is most frequently found on face, neck and back, chest, shoulders and upper arms. Acne is characterized by the formation of comedones, papules, pustules, less frequently nodules or cyst and in some cases scarring. A peak of incidents is usually between 14 to 19 years. Four major factors in its pathogenesis Increased Sebum Production
1) Keratinization of pilosebeceous duct
2) Abnormality of microbial flora
3) Production of inflammation
4) Hydration The pharmacological composition of this invention when therapeutically locally applied inhibits sebum secretion and also inhibits sweat gland secretion and provides an anhidrotic skin area. The pharmacological compositions of this invention also have mild karatolytic activity and diminish keratinization. The antibiotic properties provide a sterile surface preventing or minimizing causative bacteria p-acne, as well as microbial flora. The composition also acts as an anti-inflammatory.

The preferred treatment is with a topical pharmacological composition of a 1% to 5% (by weight) of a mixture of sodium citrate and citric acid or, alternatively with a 1% to 5% mixture of sodium oxalate and oxalic acid. Optionally, 1% to 2% salicylic acid may be added. In severe conditions 0.5% to 1% hydrocortisone may be added for a short period of time. A widely used treatment for cystic acne is direct local injection into the cyst, which is very painful and may cause leocoderma on the skin, i.e., the skin becomes depigmented. With the treatment described herein, the cystic acne is treated with 2% to 5% of the pharmacological composition along with 0.025% to 0.05% Clobetasol propionate in suitable oil free cream applied locally. Such a treatment provides excellent results to dissolve cyst.

*Pityriasis Rosea*

The pharmacological compositions of this invention may also be used for treating *Pityriasis Rosea*. *Pityriasis rosea* is an acute and self-limiting disease. The exact cause of the skin condition is unknown, probably infective in origin, affecting mainly children and young adults and characterized by distinctive skin eruption and minimal constitutional symptoms.

*Pityriasis Rosea* eruption has been associated with drugs such as arsenic, bismith, gold, captopril, ketototifen, etc. The eruption of *Pityriasis Rosea* follows a distinctive and remarkably constant pattern. Lesions are defined bright red, round or oval plaque, soon coved by fine scales. Lesions erupt in crops.

The pharmacological compositions of this invention when topically applied locally, the skin lesions subside within five to fifteen days. It is theorized that the mechanism of its action is keratolytic and anti-bacterial.

The preferred treatment is with topical pharmacological compositions of a 2% to 5% (by weight) of a mixture of sodium citrate and citric acid or, alternatively with a 2% to 5% mixture of sodium oxalate and oxalic acid. Optionally, 1% to 2% salicylic acid may be added.

Psoriasis

The pharmacological compositions of this invention may also be used for treating Psoriasis. Psoriasis is a genetically determined inflammatory and proliferative disease of skin, most characteristic lesions consisting of chronic, sharply demarcated, dull red scaly plaques. Provocative factors involved trauma, infection, sun light, metabolic factor drugs and etc.

The preferred treatment is with a topical pharmacological composition of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added.

Lichen Planus

The pharmacological compositions of this invention may also be used for treating Lichen planus. Lichen planus is an immunologically mediated disease. Commonly presented as a skin lesion that is shiny, polygonal and violates papules. The lesion varies in size from a pin point to a centimeter or more and may be closely aggregated or widely dispersed. On the surface there may be Wickham's striae. Buccal mucosa and the tongue are most often involved but the anus and genitalia may also be involved. Lichenoid drug eruptions may occur due to certain drugs, for example, mepacrine, isoniazid.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added. An oral composition may also be used for treatment.

Seborrhoeic Dermatitis

The pharmacological compositions of this invention may also be used for treating Seborrhoeic Dermatitis. It is a chronic dermatitis characterized by distinctive morphology including red sharply marginated lesions covered with greasy looking scales and a distinctive distribution in areas with a rich supply sebaceous glands namely the scalp, face and upper trunk. Dandruff appears to be the precursor of seborrhoeic dermatitis. The yeast *Malassezia furfur* is increased in seborrhoeic dermatitis. *P. ovale* is also found.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added.

Tinea

The pharmacological compositions of this invention may also be used for treating Tinea (Fungal Infections). The present compositions are suitable as broad spectrum, topical antifungal preparations for the treatment oaf variety of fungal infections that may develop on the skin and nails, or which may be present and viable on surfaces which may come in contact with skin and nails. As a result, the compositions of the present invention may be used either therapeutically to treat a pre-existing infection, or as a fungicidal disinfectant to cleanse surfaces that may harbor the fungus, thereby preventing or limiting the occurrence of infections. The compositions are used to topically treat fungal infections that may develop on the skin (dermatomycoses) as well as toe and finger nails (onychomycosis). These fungal infections, also commonly known as Tinea pedis (athlete's foot), Tinea unguium (nail infections), Tinea cruris, Tinea corporis, Tinea versicolor and candidiasis, among others, are caused by different types of fungus such as those of the gena *Trichophyton, Epidermophyfon, Microsporum* and *Candida.*

The preferred treatment is with topical pharmacological compositions of a 2% to 5% (by weight) of a mixture of sodium citrate and citric acid or, alternatively with a 2% to 5% mixture of sodium oxalate and oxalic acid. Optionally 1% to 2% salicylic acid, 5% to 10% zinc oxide may be added. An oral composition may also be used for treatment.

Oral Submucous Fibrosis

The pharmacological compositions of this invention may also be used for treating Oral Sub mucous Fibrosis. This disease can follow burns, irradiation but commonly and particularly this disease occurs due to habit of chewing of betel-nut which predisposed to oral sub mucus fibrosis. In such condition there is loss of elasticity of oral tissues. This disease is particularly found in Indian sub-continent. Pathologically there is fibrosis extending to sub mucosa and muscles. Epithelial changes included atrophy to keratosis. This disease, when severe, restricts the mouth from opening. The patient is unable to eat and even talk properly. This disease may transform into squamous cell carcinoma. Management of this disease is very difficult. Only intralesional corticosteroids injection locally has been found to help, otherwise surgery is needed. The pharmacological compositions of this invention when applied locally in a cream or in a jelly form have excellent (almost 100%) beneficial effect, resulting in the patient being able to reopen his/her of mouth to a large extent. Twenty-five (25) patients who were habitual chewers of the betel nut were the patients.

The preferred treatment is with a topical pharmacological compositions of a 2% to 10% (by weight) of a mixture of sodium citrate and citric acid or, alternatively with a 2% to 10% mixture of sodium oxalate and oxalic acid.

Amyloidosis

The pharmacological compositions of this invention may also be used for treating Amyloidosis. Amyloidosis is a disease in which there is a deposition of a proteinous substances composed of one of family of biochemically unrelated proteins which is associated with considerable dysfunction. Amyloid deposits also contain extra cellular matrix component including glycosaminoglycans and proteoglycans which may be involved in pathogenesis.

The pharmacological compositions of this invention were tested on papular (lichen) amyloidosis and upon macular amyloidosis in 24 patients and found to be effective.

Amyloidosis is classified as follows:
1) Primarily localized cutaneous Amyloidosis
2) Secondarily localized cutaneous Amyloidosis
3) Systemic Amyloidosis The pharmacological compositions of this invention are used to therapeutically treat skin (cutaneous) amyloidosis whatever the cause. My invention only treats and treated with success all skin conditions, where there is deposition of amyloid.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added.

Purpura

The pharmacological compositions of this invention may also be used for treating Purpura. Purpura is discoloration of skin or mucous membranes due to extra extravasations of red blood cells due to many causes. The skin becomes purpuric. Purpura may be caused by raised intravascular pressure. There are several types, e.g., senile purpura, corticosteroid purpura, drug purpura, contact purpura, schamberg purpura, coagulation defects purpura and etc.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally, 0.025% to 0.05 clobetasol propionate may be added to the pharmacological composition.

Discoid Lupus Erythematosus.

The pharmacological compositions of this invention may also be used for treating Discoid lupus erythematosus. This disease is an autoimmune disease characterized by eruption of scaly patches atrophy, scarring and pigmentary changes, and most frequently involving the face. The disease affects twice as many females as males.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added.

Contact Dermatitis

The pharmacological compositions of this invention may also be used for treating Contact dermatitis. Any antigen that comes in contact with skin may react with the skin causing contact dermatitis. It may be either primary irritant contact dermatitis or primary allergic contact dermatitis. For example, there is shoe dermatitis, hair dye contact dermatitis, nickel dermatitis, washing powder dermatitis, etc. The skin becomes scaly, pigmented and itchy and in some cases oozing.

The preferred treatment is with topical pharmacological compositions of a 1% to 10% (by weight) of a mixture of sodium citrate and citric acid or, alternatively with a 1% to 10% mixture of sodium oxalate and oxalic acid. Optionally 2% to 4% salicylic acid and/or 0.025% to 0.05% clobetasol propionate and 5% to 10% zinc oxide may be added as for sun screening agent and also for as soothing effect.

Hair and Skin Shiner

The pharmacological compositions of this invention may also be used as a hair and skin shiner. The compositions make the hair and skin shine, reflect the light causing an attractive look. This invention may be incorporated in shampoo and in face cream.

The preferred treatment is with topical pharmacological compositions of a 2% to 10% (by weight) of a mixture of sodium citrate and citric acid or, alternatively with a 2% to 10% mixture of sodium oxalate and oxalic acid.

Mollascum Contagious.

The pharmacological compositions of this invention may also be used for treating Mollascum contagious. This is viral infection of skin caused by an unclassified member of poxviridae in mollascum contagiousam lesion, characterized by papules and nodules. Its general treatment included cryotherapy, squeezing its forceps (a painful procedure), application of silver nitrate or phenol with stick and etc.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid may be added.

Herpes Simplex

The pharmacological compositions of this invention may also be used for treating Herpes simplex. This is viral infection is caused by herpes virus hominis (herpes simplex virus, HSV). It is a common infection in men. Skin shows vesicles presenting as white plaques are present. Skin, tongue, buccal mucous membrane, palate, genital area and etc. are involved.

The preferred treatment is with topical pharmacological compositions of a 2% to 5% (by weight) of a mixture of sodium citrate and citric acid or, alternatively with a 2% to 5% mixture of sodium oxalate and oxalic acid. Optionally 1% to 2% salicylic acid and 5% to 10% zinc oxide may be added.

Paronychia

The pharmacological compositions of this invention may also be used for treating Paronychia. Paronychia is a painful full swelling of nail folds. It commonly occurs in persons whose hands are excessively exposed to water. It may result from local injuries for example nail biting, splits or there may be no preceding injuries. It is a common complaint and is usually due to bacterial infection including staphylococcal, other organisms involved in it may be streptococci, *pseudomonas, proteus vulgars* and it may also be due to other causes for example fungal infection, *Candida albicans* infection, etc.

The preferred treatment is with topical pharmacological compositions of a 2% to 5% (by weight) of a mixture of sodium citrate and citric acid or, alternatively with a 2% to 5% mixture of sodium oxalate and oxalic acid. Optionally 2% to 4% salicylic acid may be added.

EXAMPLES

Preparation Active Composition

An equal amount of pharmaceutical grade sodium bicarbonate and citric acid by weight was placed in a sterile plastic container in an open room with a temperature at about 25 degree Celsius. The composition was mixed until a uniform mass was formed. A sufficient amount of purified sterile water was poured slowly into the mass to allow the reaction of sodium bicarbonate and citric acid. The mixture was left standing for 24 hours to allow the water and carbon dioxide to evaporate and for the product to dry. The mixture was again stirred to allow carbon dioxide and water vapors to further escape. A white crystalline and odorless powder was obtained. The final product contained 87% sodium Citrate and 13% citric acid as active ingredients. The measured pH of final product was 6. This solid composition was crushed and ground to a fine powder to produce an active composition that was pharmaceutically and physiologically acceptable, hereinafter the "pharmacological composition".

Sodium Citrate-Citric Acid Mixture

Stoichiometric Formulation Ratio:

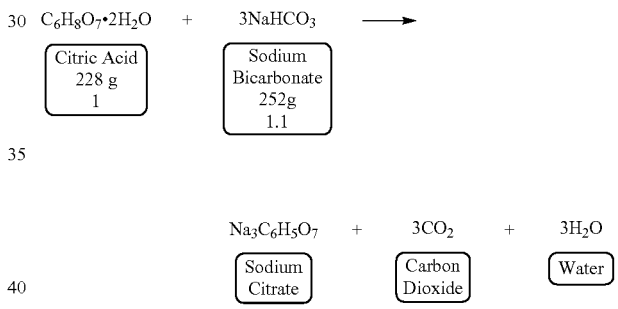

Method of Producing Active Composition:

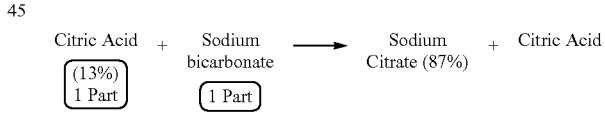

Chemical Equation with Structural Formulas:

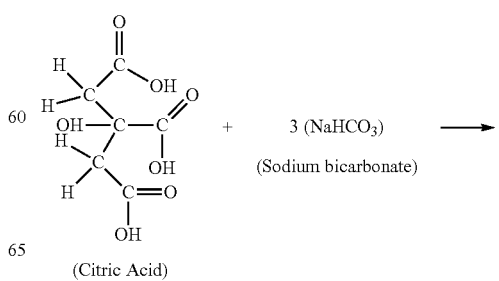

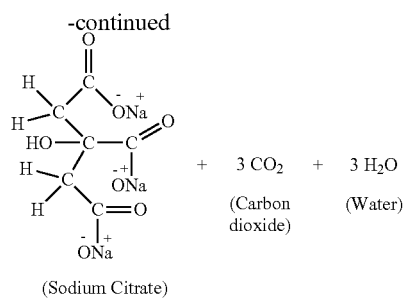

(Sodium Citrate) + 3 CO$_2$ (Carbon dioxide) + 3 H$_2$O (Water)

Structural Formulae of Active Ingredients:

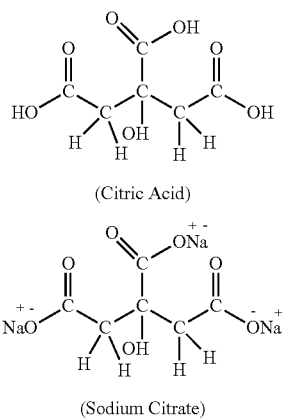

(Citric Acid)

(Sodium Citrate)

In Vitro Study

Summary:

The goal was to determine the susceptibility and activity of the powdered pharmacological composition produced on different bacterial strains at different concentration. The composition was a mixture of sodium citrate (stoichiometric ratio) and citric acid with the percentage of sodium citrate 87% and citric acid 13%, The procedure was to apply the powdered pharmacological composition of sodium citrate and citric acid to infectious bacterial strains and to determine susceptibility and activity of the pharmacological composition as anti-bacterial agent.

1. Material & Method:

Different infectious bacterial strains from different infected sites were selected, including pathogenic gram positive and gram negative bacterial strains. The activity of the powdered pharmacological composition on different bacterial strains was determined by applying it at different concentrations on various strains. In this study significant antimicrobial was observed when we used 300 mg and 500 mg of the pharmacological composition in dry powdered form.

The powdered pharmacological composition, i.e., a mixture of sodium citrate and citric acid with the percentage of sodium citrate 87% and citric acid 13%, was applied to infectious bacterial strains, including Gram Positive Organism (*Staphylococcus aureus Streptococcus* species and *Streptococcus* Gp D) and gram negative bacteria (*E. toll, Klebsiella* species, *Moragnella* species, *Enterobacter* species, *Serratia* species, *Salmonella typhi, Proteus* species) to determine susceptibility to anti-microbial activity of the composition.

A wire loop method was used to inoculate the bacteria on media plates. MacConkey Agar (Merck, Germany) was used for culturing of gram negative organism and blood Agar Media (Oxoid, England) was used for culturing the gram Positive Organism. For Confirmation and Identification of the organism, biochemical tests were done. For gram Negative Organism we used Triple Sugar Iron Media (Oxoid, England), Citrate Agar (Merck, Germany) Sulphide Indole motility media (Merck, Germany) Urea Agar (Oxoid, England) and for Gram Positive Organism we used Catalase test, Novabisin disk and manitol Salt Agar for Identification of *Staphylococcus aureus* and we also performed tube Coagulase test and for *Streptococcus* we did gram staining and Catalase test (showed negative Result).

2. Anti-Microbial Susceptibility Testing

The Gram Positive Organism tested:
*Staphylococcus aureus.*
*Streptococcus* species.
*Streptococcus* gp D.

The Gram Negative Organism tested:
a. Lactose fermenting bacteria:
*E. coli.*
*Klebsiella* species
*Enterobacter* species
b. Non-Lactose fermenting bacteria:
*Pseudomonas aeruginosa.*
*Proteus* species
*Morganella* species.
*Serratia* species.
*Salmonella* species.

In the present study anti-microbial susceptibility testing was done on Mueller Hinton Agar (Oxoid, England) using disk diffusion (Kirby Bauer's) technique. This method was done according to Clinical and Laboratory Standards Institute (CLSI) guideline to determine susceptibility of microbial agents.

Description:

The standard method used for determination of antimicrobial susceptibility is the disk diffusion procedure of Macfarland turbidity (Provided Powder used in replacement of disk)

Material Required:
Suitable agar & broth.
Provided Powder.
Sterile Cotton Swab.
Wire loop.
Medium: Mueller Hinton Agar (Oxoid, England)
Broth: Sterile peptone water (Oxoid, England)

Procedure:
Inoculum:
a) The inoculums were prepared by transferring a few identical colonies of different organism from the primary growth of Gram Negative (*Pseudomonas aeruginosa, E. coli Klebsiella* species, *Enterobacter* species, *Moragnella* species, *Proteus* species, *Serratia* species, *Salmonella* species) and Gram Positive (*Staphylococcus aureus, Streptococcus* gp D and *Streptococcus* species) with a wire loop in 2 ml of Peptone water (already filled in Sterile tube).
b) Incubate the Suspension at 35° C. for 10-15 minutes.
c) A sterile Swab applicator was dipped into the Culture Suspension. Excess suspension was removed by rotating it against side wall of tube, then streak on entire surface of medium in 3 different directions, by rotating the plate at 60° C. angle.

Placement of Pharmacological Composition (Antimicrobial Agent) (Powder) at Different Conditions and Concentrations:

After Streaking, the inoculum was allowed to dry for at least 5 minutes and inoculated with the powdered composition.

Pharmacological composition (antimicrobial agent) powder was applied: (50 mg)

For *Staphylococcus* (Resistant Strain and Sensitive strain:2 strains used), *Streptococcus* gpD *Streptococcus* species, *Pseudomonas aeruginosa*, *E. coli Klebsiella* species, *Serratia* species, *Morganella* species, and *Proteus* species)

Pharmacological composition (antimicrobial agent) powder was applied: (500 mg)

For *Klebsiella* species, *E. coli*, *Streptococcus species*, *Pseudomonas aeruginosa*, *Staphylococcus aureus Serratia* species, *Morganella* species, *Enterobacter* species and *Proteus* species.

Pharmacological composition (antimicrobial agent) powder was applied: (300 mg)

For *Klebsiella* Species, and different strains of *E. coli*.

The same procedure was used for 1000 mg

Incubation:

After the direct placement of the pharmacological composition (antimicrobial agent) was applied (50 mg) the concentrated disk on Mueller Hinton plates should be incubated aerobically at 35° C. for overnight.

Precautions:

For the proper interpretation of the results:
1. The suspension should always be made from pure culture and not from mixed culture.
2. The size of inoculum is uniform (avoid heavy/light inoculum).
3. The incubation condition must be of appropriate temperature and atmosphere.
4. The depth of the medium 4 mm (Approx. 25 ml medium in 100 mm plate)
5. The incubation period should not be less than 8 hrs. or more than 24 hrs.

Results:

In this study the organism showed different activities.

TABLE 1

Direct Antimicrobial Agent (Powder) applied at 50 mg Experiment.

| Bacteria | Used Quantity of antimicrobial agent | Result. |
|---|---|---|
| Gram Positive Bacteria: | | |
| *Staphylococcus aureus* | | |
| Strain 1 | 50 mg | Showed Activity |
| Strain 2 | 50 mg | Showed Activity |
| *Streptococcus* gp D | 50 mg | No-Activity Observed |
| *Streptococcus* species | 50 mg | No-Activity Observed |
| Gram Negative Bacteria: | | |
| *E. coli* | 50 mg | No-Activity Observed |
| *Klebsiella* species | 50 mg | No-Activity Observed |
| *Serratia*, species | 50 mg | No-Activity Observed |
| *Morganella* species | 50 mg | No-Activity Observed |
| *Proteus* species | 50 mg | No-Activity Observed |
| *Pseudomonas aeruginosa* | 50 mg | No-Activity Observed |

TABLE 2

Direct Antimicrobial Agent (Powder) applied at 500 mg.

| Bacteria | Used Quantity of antimicrobial agent | Result | Zone of inhibition Size |
|---|---|---|---|
| Gram Positive Bacteria: | | | |
| *Staphylococcus Aureus* | 500 mg | Showed Activity | 22 mm |
| *Streptococcus* species | 500 mg | Low effect showed | — |
| Gram Negative Bacteria: | | | |
| *E. coli* | 500 mg | Showed Activity | 25 mm |
| *Klebsiella* species | 500 mg | Showed Activity | 28 mm |
| *Pseudomonas aeruginosa* | 500 mg | Showed Activity | 43 mm |
| *Serratia* species | 500 mg | Showed Activity | 30 mm |
| *Morganella* species | 500 mg | Showed Activity | 30 mm |
| *Enterobacter* species | 500 mg | Showed Activity | 28 mm |
| *Proteus* species | 500 mg | Showed Activity | 25 mm |

*Zone size showed variation due to use of dry loose form of powder.

TABLE 3

Direct Antimicrobial Agent (Powder) applied at 300 mg.

| Bacteria | Quantity of antimicrobial agent | Result. | Zone of Inhibition Size |
|---|---|---|---|
| Gram Negative Bacteria: | | | |
| *E. coli* | 300 mg | Showed Activity | 45 mm |
| *Klebsiella* species | 300 mg | Showed Activity | 35 mm |

*Used different strains in of E. coli and Klebsiella species in Table 2 & 3

Discussion:

This study demonstrates the activity of the powdered anti-microbial agent, i.e., the pharmacological composition, against micro-organisms. This microbial agent (powder) or pharmacological composition also worked against those organisms which are normally highly resistant against other antimicrobial agents. Those organisms include *Pseudomonas aeruginosa*, *Staphylococcus aureus*, *Streptococcus* gp D.

In the first set of tests we applied the antimicrobial agent, i.e., pharmacological composition, in very low quantities (50 mg). Minimal activity was observed against Gram Positive (*Staphylococcus aureus Streptococcus* gp D *Streptococcus* species) and Gram Negative Strains (*Pseudomonas aeruginosa*, *E. coli Klebsiella* species, *Serratia* species, *Moragnella* species, *Proteus* species).

In the second set of tests condition we increased the quantity of antimicrobial agent (powder)—pharmacological composition—to 500 mg quantity of the powder which showed activity against bacteria Gram Positive bacteria (*Staphylococcus aureus Streptococcy* species) and Gram Negative bacteria (*Klebsiella* species, *E. coli Pseudomonas aeruginosa*, *Serratia* species, *Moragnella* species, *Proteus* species, *Enterobacter* species).

In the third set of tests we used different strains of *Klebsiella* species and *E. coli* and applied 300 mg antimicrobial agent (powder)—pharmacological composition— which showed activity against those bacterial strains.

Conclusions:

In this study minimal activity was observed after applying 50 mg of the anti-microbial agent. Significant zone sizes of inhibition were observed when the pharmacological composition was applied directly at 500 mg and 300 mg potency in powdered form.

It is believed that the mode of action of the pharmacological composition is to inhibit, topoisomerase enzyme which inhibits bacterial cell replication.

Clinical Trials

Oral Treatment of Bacterial Infection

I applied the pharmacological composition as anti-bacterial agent in numerous patients. The pharmacological composition contained 87% sodium Citrate and 13% citric acid as active ingredients. The measured pH of the final product was 6. This solid composition was crushed and ground to a fine powder to produce an active composition that was pharmaceutically and physiologically acceptable, hereinafter the "pharmacological composition" and then encapsulated, hereinafter the encapsulated pharmacological composition. Included herein are exemplary results from ten (10) patients.

Oral Application of Pharmacological Composition:

| Patient A | |
|---|---|
| Gender | Male |
| Age | 28 years |
| Diagnosis | Typhoid |

Present Complaint:

Patient complains of fever for the past week. Patient states that the fever fluctuates between highs and lows, and sometimes remains low but it does not reach normal. The patient is lethargic and feels week. Patient has also complained of abdominal pain for the past two days.

Examination:

His fever is 99° F.; blood pressure is 120/70 mm of Hg. A Typhidot test for typhoid was positive, ESR 55 mm/hr., CBC (complete Blood Picture) report shows Hb 9.5 g/dl, TLC 14×10$^9$/L, Blood Culture report shows *salmonella* typhoid. Typhoid fever is confirmed.

Treatment:

The patient was given 500 mg of encapsulated pharmacological composition thrice daily and advice to take half an hour after food and revisit after 5 days.

Second Visit:

Patient visited five days after initial visit to state that his fever subsided but not completely. The patient also said that his overall condition has improved. Patient was given same 500 mg encapsulated pharmacological composition and advised to continue to take thrice a day and revisit after five days.

Third Visit:

Patient revisited five days after the previous date and indicated that his fever had completely subsided and that his weakness and other illness like condition had also subsided. The patient was told to repeat the same treatment of 500 mg of the encapsulated pharmacological composition thrice a day and advised to complete the therapy for further five days and then revisit for a blood culture and sensitivity report.

Fourth Visit:

The patient was seen nine days after the Third Visit with complete satisfaction, as there is neither fever nor any other illness like condition. A blood culture and sensitivity report showed no bacterial growth. All treatment was stopped.

| Patient B | |
|---|---|
| Age | 31 years |
| Gender: | Female |
| Diagnosis: | Tonsillitis |

Present Complaint:

Patient complained that she was suffering from severe tonsillitis for 15 days. The patient complained of severe pain, itching, and irritation in throat. She developed hoarseness of voice. The patient said that she had chronic history of tonsillitis for the last 8 years. The condition remained off and on. When she developed a severity in her disease a consultant advised her broad spectrum antibiotic injection. After getting injections for at least 15 days, she obtained relief for 1 to 2 months.

Examination:

Her throat was severely inflamed and there were enlarged tonsils with pustules with oozing purulent pus. The tonsils are grossly inflamed.

Treatment:

The patient is given 500 mg of the encapsulated pharmacological composition twice a day and advised to return after 5 days.

Second Visit:

Patient visited 5 days after her previous visit. Her tonsillitis and other inflammatory condition were reduced by about up to 50%. The patient was again advised to continue 500 mg encapsulated pharmacological composition twice a day and revisit after 5 days.

Third Visit:

The patient visited 5 days after her previous visit. Her severe inflammatory condition and severe tonsillitis signs and symptoms were almost totally subsided; her hoarseness of voice and other complaints also subsided. To be on the safe side, the patient was again advised to continue 500 mg capsules twice daily for 5 days more since she had been suffering in this disease for the last 8 years. After taking this last dose she was told there was no need for additional visits unless she had complaints.

Fourth Visit:

Patient visited 6 months after her last visit and was very happy and saying that after every 2 to 3 months she used to develop tonsillitis and used to get antibiotic injections. She has not developed tonsillitis her last treatment.

Patient: C

Age; 42 years

Gender; female

Diagnosis; UTI

Present Complaint:

Patient complains of burning micturition for the last 10 days.

Examination:

Patient looked ill and appears to be tense and have 99° F. fever. A detailed report on urine shows pus cells 15-20/field and culture and sensitivity report shows growth of *E coli*.

Treatment:

Patient was told to take 500 mg of encapsulated pharmacological composition twice a day and advised to revisit after 5 days.

Second Visit:

Patient visited 5 days after the previous date and said that now she is feeling relief and now there is no burning micturition. Patient was advised to continue 500 mg encapsulated pharmacological composition for an additional 5 days and at the end of 5th day come with investigation report of urine detailed report on culture and sensitivity.

Third Visit:

Patient visited 8 days after her last visit and said she was satisfied and that there no burning micturition, fever or other complaints. Her urine report showed no bacterial growth. Her treatment was stopped.

Patient: D
Age: 55 years
Gender: female
  Diagnosis:
  Cholecystitis
  Present Complaints:

Patient complained of severe pain in right hypochondrium region for 8 days. Upon examination of investigations report, ESR 49. Ultrasound of upper abdomen shows cholecystitis and cholelithiasis Examination:

Patient looked tense and anxious. Patient complained of nausea and vomiting. Upon examination of abdomen there was tenderness on the right hypochondrium.

Recommendations:

Patient was advised to take 500 mg encapsulated pharmacological composition twice a day and revisit after 5 days.

Second Visit:

Patient visited 5 days after previous visit and said there was relief in her pain and the nausea and vomiting had subsided. Patient was advised to continue the same remedy and dose for an additional 5 days.

Third Visit:

Patient visited 5 days after the previous visit with complete relief in pain, nausea, vomiting and others sign and symptoms. Patient is again told to do the same treatment as previously, 500 mg encapsulated pharmacological composition for an additional 5 days to be on the safe side and advised to revisit after 5 days with an ultra sound report.

Fourth Visit:

Patient visited 5 days after previous visit with ultra sound report which was normal, without cholecystitis. The treatment was stopped.

Patient: E
Age: 50 years
Gender: male
  Diagnosis:
  Carbuncle
  Complaint:

Patient had a case of diabetes mellitus since 12 years and is on anti-Diabetic treatment. Twenty days prior to his visit he developed a nodule on the back of his neck which was gradually increasing in size and acquired big area and which started oozing and later on there was pus discharging from multiple orifices and severe pain.

Examination:

There was a big lesion with multiple orifices with pus discharge and marked inflammation.

Investigation Report:

Shows high side Fasting and Random blood sugar.

Recommendations:

Patient was given 500 mg 500 mg encapsulated pharmacological composition to take four times a day half an hour after food and advised to revisit after 5 days.

Second Visit:

Patient's lesions were improved and there was a declination in inflammation, oozing and pus discharge. The patient had achieved some relief. The patient was advised to continue the same treatment of 500 mg encapsulated pharmacological composition four times a day and was advised to revisit after 5 days Third Visit:

The patient visited 5 days after the previous visit and was greatly satisfied. There was a remarkable declination of the lesion area, remarkable declination in oozing and pus discharge and the inflammatory condition. The patient had achieved some relief. The patient was advised to continue the same treatment of 500 mg encapsulated pharmacological composition three times a day and was advised to revisit after 5 days.

Fourth Visit:

Patient visited 5 days after the previous visit and was fully satisfied. Upon examination the lesion was completely cure. There was no inflammatory condition, oozing or pus discharge. There remained only a very peanut size dried nodule. To be on the safe side The patient was advised to continue the same treatment of 500 mg encapsulated pharmacological composition three times a day and for 5 days and advised that he need not return but to get proper treatment for the diabetic mellitus, as he was cured now.

Patient F
Gender: male
Age: 12 years
  Diagnosis:
  Chalazion
  Complaint:

small, soft reddish nodule on right upper inner lid with slight pain and pus discharge for 10 days. He received treatment in the past, but there was no relief.

Examination:

There was a markedly inflammatory soft peanut size nodule with slightly discharging purulent pus on right upper inner side of lid with conjunctivitis eye.

Recommendations:

Patient was given 250 mg the crushed and ground pharmacological composition containing 87% sodium citrate and 13% citric acid in neutral syrup thrice a day half an hour after food and was advised to revisit after 5 days.

Second Visit:

Patient visited 5 days after previous visit and his mother said that he has obtained substantial relief, the lesion was reduced and the redness in his eye also declined. Upon examination the nodule was reduced, pus discharge had ceased, and the conjunctivitis was in decline. The patient was advised to repeat the treatment for another 5 days, i.e., 250 mg the crushed and ground pharmacological composition containing 87% sodium citrate and 13% citric acid in a neutral syrup thrice a day half an hour after food and was advised to revisit after 5 days.

Third Visit:

The patient visited 5 days after previous visit and was satisfied. There was no complaint of pain, redness, nodule, discharging pus, or conjunctivitis in eye. There appeared to be a remnant of a lesion. The patient was given same remedy with same dose for an additional 5 days to be on safe side, advised to stop treatment after that and that there was no need to visit again because you are cured.

| Patient G | |
|---|---|
| Gender | Female |
| Age | 36 years |
| Rx | Paronychia |

Complaint:

Patient complains of pain, swelling and pus discharge from the nail fold of right index finger for about one week.

Examination:

There was swelling and purulent pus discharge and an inflammatory condition. The case was diagnosed as Paronychia.

Recommendations:

Patient was given 500 mg encapsulated pharmacological composition twice a day and advised to revisit after 5 days.

Second Visit:

Patient visited 5 days after previous visit and had achieved more than 75% relief. Upon examination the swelling, discharging pus, inflammatory condition and pain had subsided to a large extent. Patient was given 500 mg encapsulated pharmacological composition twice a day and advised to revisit after 5 days.

Third Visit:

Patient visited 5 days after the previous visit and was fully satisfied as there were neither complaints of pain. Upon examination there was no swelling, pus discharge or inflammatory lesions. The patient was completely cured and treatment was stopped Patient: H
Gender: Male
Age: 52 years
Diagnosis:
Acute exacerbation of chronic bronchitis.
Complaints:

Patient complained of a history of chronic bronchitis for the last three years where he gets attacks of fever and severe attacks of cough with purulent sputum and preventing him from obtaining sleep for the past year. He has a history smoking for thirty years. Two months ago the symptoms were not present but as the weather changed he has again developed fever, cough with purulent sputum for the last week. He was told that he has an acute exacerbation of chronic bronchitis.

Examination:

Patient had a fever, on auscultation there is wheezing and crepitation on chest.

Recommendations:

Patient was given 500 mg encapsulated pharmacological composition four times a day half an hour after food and advised to revisit after five days.

Second Visit:

Patient revisited five days after previous visit and says that he obtained some relief but still has a cough with purulent sputum. He was still running a fever but the temperature slightly subsided. Patient was again given 500 mg encapsulated pharmacological composition four times a day half an hour after food and advised to revisit after five days.

Third Visit:

Patient visited five days after the previous visit and was highly satisfied in that he had obtained much greater relief and there was no fever. However, his cough and purulent sputum had only somewhat subsided, but now sleeps deeply and comfortably. Patient now complained of dizziness and was given anti-motion therapy. Patient was again given 500 mg encapsulated pharmacological composition three times a day half an hour after food and advised to revisit after five days.

Fourth Visit:

The patient visited five days after previous visit with full satisfaction and says that now he was in relief and there was no fever, cough or sputum nor complaint of dizziness after taking anti-motion drug. To be on the safe side the patient is again given same 500 mg encapsulated pharmacological composition but now only twice a day for an additional five days and then stop treatment for he is now cured.

Patient: I
Gender: female
Age: 25 years
Diagnosis:
cellulitis (skin and soft tissue infections)
Complaint:

Patient is 24 weeks pregnant and complains redness and pain on upper front of left thigh and also complains of fever for past five days.

Examination:

There was redness and an inflammatory condition on the front of left thigh. On touching the lesion, it was warm and tender and there was tenderness.

Recommendations:

The patient was given 500 mg encapsulated pharmacological composition twice a day, half an hour after food and advised to revisit after five days.

Second Visit:

Patient visited five days after previous visit with declination of lesion and inflammation tenderness. Her fever had subsided. The patient had complained of slight nausea and vomiting. The patient was given 500 mg encapsulated pharmacological composition twice a day, half an hour after food. She was also given nausea and vomiting anti-emetic drug. Patient was advised to revisit after five days.

Third Visit:

Patient visited five days after previous visit with marked declination of signs and symptoms. There was no fever, tenderness, pain or inflammatory condition. There was still a complaint of nausea and vomiting and she was given anti-emetic. Patient for safety was advised to repeat the 500 mg encapsulated pharmacological composition twice a day, half an hour after food for an additional five days to reduce all signs and symptoms.

Patient: J
Gender: male
Age: 16 years
Diagnosis:
Sub acute appendicitis
Complaints:

Patient complained of an on and off pain in right hypochondrium for the last three days. The patient also complained of nausea with episodes of pain. The patient also complained of fever for the past three days. Patient also complained of the same symptoms twenty days back.

Examination:

There was tenderness on the right hypochondrium and there was a low grade fever also.

Recommendations:

The patient was given 500 mg encapsulated pharmacological composition twice a day, half an hour after food and advised to revisit after five days.

Second Visit:

The patient revisited five days after previous visit. The signs and symptoms had subsided. Upon examination there was less tenderness and there was also no fever. The patient was given 500 mg encapsulated pharmacological composition twice a day, half an hour after food and advised to revisit after five days. The patient was also advised to consult a General Surgeon for his opinion because the appendix might burst, which might cause peritonitis and poisoning with a fatal outcome. The therapy recommended herein reduced all signs and symptoms and had arrested the growth of bacteria, reducing inflammation.

Third Visit:

Patient revisited five days after previous visit with complete satisfaction. All signs and symptoms were reduced. The surgeon advised that if he again feels severe pain than he will operate to remove the appendix. If there are no complaints there is no need to operate. All therapy stopped.

Side Effects and Drug Interaction Observed

No serious side effects were observed in any patients. The only side-effects observed, were nausea and vomiting and some dizziness in about 0.5% of the patients. One in 500 patients developed a minor allergic reaction which subsided when treated with an anti-histamine drug. There were no drug interactions noted with anti-coagulant drugs. No serious adverse effects were observed in patients or any life-threatening conditions as Steven-Johnsons syndrome or anaphylactic shock with oral therapy.

EXAMPLES

Treatment of Deformed Nails

An embodiment of this invention relates to ameliorating, preventing and/or treating nail deformity, slow nail growth/retardation due to either systemic or local skin diseases. The pharmacological compositions of this invention may be used to enhance the growth of nails which are broken before attaining its normal length.

The preferred treatment is with topical pharmacological compositions of a 2% to 10% (by weight) of a mixture of sodium oxalate and oxalic acid. The method of treatment of such nail growth symptoms comprises topically applying to the nails a composition comprising a mixture of sodium oxalate and oxalic acid with specific ratio by percentage, by weight and a physiologically acceptable carrier vehicle. The highly preferred composition is a mixture of 78.44% sodium oxalate and 21.56% oxalic acid. A preferred range is about 73% to about 83% Sodium oxalate and about 17% to about 27% oxalic acid. It is to be understood however that various weights and ratios of sodium oxalate and oxalic acid may be used as long as a safe and efficacious pharmacological composition is produced. Optionally, the composition applied consists of a mixture of sodium oxalate and oxalic acid and an effective amount of hydrocortisone, e.g., about 1% by weight of hydrocortisone.

The method of this invention is effective, low cost, and easily applied. The composition used is easy to manufacture as demonstrated herein and is effective in the treatment of deformed nails, e.g., nail diseases, to ameliorate, prevent and/or treat such diseases.

The method for treating the deformed nails and nail diseases herein comprises topically administering or applying a composition, comprising a sodium oxalate and oxalic acid mixture with specific ratio by weight and percentage to the nails of a mammal, typically a human. More specifically, the method comprises applying a pharmacological composition to the patient's fingers or toe nails. The amount of the composition applied is a therapeutically effective amount of the composition that will ameliorate, prevent and treat nail diseases/deformed. The patient should avoid contacting his/her eyes with his/her fingers after treatment.

Pharmaceutical Carrier

Examples of the pharmaceutical carrier and the method of preparation that may be used are provided herein.

A. Oil and water base vehicle (base) preparation (100 grams on small scale):

Vessel A—Take 75 grams purified and sterile water in suitable container like stainless steel vessels and heat it to 70° C.

Vessel B—Take 25 gram of a pharmaceutical grade emulsifying wax and melt it by heating up to 70° C. in a water bath.

Mix the heated water into heated emulsifying wax stirring slowly until the mixture is uniform and the temperature of mixture decreases to about 35° C. then cool. The pharmaceutical carrier thus contains 25% emulsifying wax and 75% water by weight.

Pharmacological Composition

Composition A:

5% sodium oxalate and oxalic acid mixture incorporated in the pharmaceutical carrier, i.e., 25% % emulsifying wax and 75% water. Optionally, a preservative may be added.

Composition B:

5% sodium oxalate and oxalic acid mixture and 1% hydrocortisone incorporated in the pharmaceutical carrier, i.e., 25% % emulsifying wax and 75% water.

Treatment Procedures and Clinical Results

Patient: A

Age: 36
Gender: Male
Status: Married, low socio-economic
History or Complaints of Patient:

Patient complains that his nails were normal with natural shape two years back, then gradually the nails began to develop pin head size depressions on nails surface of two nails. With the passage of time, gradually these depressions increased in other fingers nails also and within the period of 3 years, most of the nails have pin head size depressions. Patient does not give any history of depression in toe nails On Examination of Patients:

On examination of the patient, no existing lesions or signs were found of any existing skin disease, although his skin appears to be dry. There was no history of any systemic disease or skin disease. On examination of the nails of the fingers pitting was observed on most of his nails but there were no depressions (pitting on toes nails) except that his all nails were rough and dry.

Diagnosis:

Diffused pitting on the finger nails.

Treatment and Advice:

Patient was given Remedy A and advised to apply it locally on the affected nails twice a day and revisit after 20 days.

Patient $2^{nd}$ Visit:

Patient revisited 20 days after the first visit to say that his nail depressions were declining. On examination his pitting nails were filling. The patient was given the same Remedy A to apply in the same manner as previously and advised to revisit after 20 days.

Patient $3^{rd}$ Visit:

Patient visited one month after previous date. 75% of the nails pitting depressions were filled. Patient was again given same Remedy A with the advice to revisit after one month Patient 4th Visit:

The patient visited one month after his previous visit and was quite happy because all the nail depressions were substantially filled and his nails were shining. On examination 90% of the pitting was filled. The patient was again given the same Remedy A and advised to revisit after one month.

Patient 5$^{th}$ Visit:

Patient revisited one month after the previous visit. All nail depressions were almost completely filled. Examination revealed that approximately all depressions had disappeared and the nails had luster and were shining. The patient treatment was stopped and the patient was advised to keep his nails moisturized.

Patient: B

Age: 21
Gender: Female
Status: Unmarried, College student.
History or Complaints of Patient:

Patient complains of that her nails were fine 6 years ago when she developed a depression in the middle of the right thumb nail which gradually increased in size to form a canal like structure in the nail. Subsequently fine cracks extended from the canal like structure to the edges of the nail on each side.

On Examination of Patient:

On examination of all nails of the hands and feet only the right thumb nail shows a canal like depression and the cracks projecting towards and reaching the edges of the nail on each side. Her history did not reveal any skin or systemic diseases.

Diagnosis:

median nail dystrophy of heller.

Treatment and Advice:

Patient was given Composition A and advised to apply locally twice a day and revisit after one month.

Patient 2$^{nd}$ Visit:

Patient visited one month after the first visit and said that canal and cracks are filling. On examination of the affected nail, canal and cracks were filled up to 40%. Patient was advised to revisit after one month again.

Patient 3$^{rd}$ Visit:

Patient revisited one month after the previous visit and was very happy to say that she is getting cured and the canal and cracks are being filled. On examination there was 70% of filling of depressed nail. The patient was given the same Composition A and advised to revisit after one month.

Patient 4th Visit:

Patient revisited one month after the previous visit. Her depressed nail canal was substantially filled. On examination, there was 90% filling of affected nail. She was given again the same Composition A to apply in same manner as previous and advised to revisit after one month.

Patient 5$^{th}$ Visit:

On her fifth visit one month after the previous visit the nail canal and cracks were filled completely filled. Treatment was stopped and she was advised to return in one year.

Patient 6$^{th}$ Visit:

Patient came one year after the last visit. She was 100% cured as it was at the time last attended. There were no developments of any canal or cracks.

Patient: C

Age: 12
Gender: Male
Status: Student of class 5, High socioeconomic
History or Complaints of Patient:

Mother of patient states that her son nails of fingers and toes do not grow normally and does not increase in size as others grow. She complains that these nails are not broken but have slow and limited growth. She said that after 2 to 3 months, it grows slightly but growth is restricted.

On Examination of Patients:

On examination of patient, nails of child of hands and toes are below normal growth. On examination of patient, there is no lesion in skin which could indicate any sign of skin disease. Mother does not give any history of systemic disease except that patient appears to be anemic.

Diagnosis:

Slow rate of growth of nails of hands and Toes

Treatment and Advice:

Patient is given Composition B to apply locally twice a day and revisit after 15 days Patient 2$^{nd}$ Visit:

Patient revisited 15 days after the first visit. Mother says that there has been an improvement in growth. Patient is given the same Composition B to apply twice a day in the same manner and revisit after one month.

Patient 3$^{rd}$ Visit:

Patient revisited one month after the previous visit. Mother says that his nails of toes and fingers are growing and the size of nails has been increased. Patient is given the same Remedy B to apply twice a day and revisit after one month.

Patient 4th Visit:

Patient revisited one month after the previous visit. His nails of hands and feet have become excellently increased in size. Mother says that now she is cutting his nails. Patient is given now Composition A to apply twice a day and revisit after one month.

Patient 5$^{th}$ Visit:

Patient visited one month after the previous date and now the nails have become normally growing and increasing in size as per mother says. On examination of nails, nails had become normally grown. Patient is given again Composition A to apply locally twice a day and afterwards stop the medicine. Mother is also directed to revisit anytime if she feels that after the stoppage of medicine if growth is slow.

Patient 6$^{th}$ Visit:

Patient visited 6 months after the previous date to say that his nails are growing normally.

Patient: D

Age: 17
Gender: Female
Status: student of first year college
History of Complaint of Patient:

Patient states that her nails were in normal texture three years back while started to develop pin head depression of hand nails fingers. With the passage of time, these depressions developed in other nails also. Patient also gives the history of loss of hair on scalp at three spots.

On Examination of Patients:

On examination of nails of patients, there were pin head depressions in fingers nails. On examination of her skin, there was loss of hair at three spots. Patient did not have any history of a systemic disease.

Diagnosis:

Pitting on nails of hands due to the disease Alopecia areata

Treatment and Advice:

Patient is given Composition B to apply locally on affected nails twice a day and advised to re-visit after 20 days.

Patient $2^{nd}$ Visit:

Patient visited 20 days after the first visit and says that her depressions of nail are appearing to be filled. On examination, of her nails depressions were reduced slightly. She is advised to revisit after one month. She is given same Composition B to be applied locally twice a day in same manner as previously.

Patient $3^{rd}$ Visit:

Patient revisited one month after the previous date with marked improvement. On examination of her nail, depressions were filling. Patient was given same Composition B and advised to revisit after one month and apply the medicine in same manner as previously.

Patient 4th visit:

Patient visited one month after the last visit with excellent marked improvement. Patient is given Composition A to apply in same manner locally twice a day and revisit after 15 days.

Patient $5^{th}$ Visit:

Patient revisited one month after the last visit with complete cure and there were no pitting depressions in any of the nails. The treatment is now stopped and advised to revisit if he feels any depression.

Patient $6^{th}$ Visit:

Patient visited 7 months after the last visit to complain that she is again developing depression in two nails. She is again given the Composition B to apply only at night in all fingers nails and visit after 6 months.

Patient: E

Age: 12
Gender: Female
Status: Student, Low socio-economic
History or Complaints of Patient:

Mother of child complains that nails of fingers and toes of her daughter are flat rather than convex and are adherent to nail beds since her childhood and even there is no shining in her nails.

On Examination of Patients:

On examination of patient, her fingers and toe nails are flat and lusterless. By examining her whole body skin, there found no any sign of skin disease. Patient mother does not give any history of current or previously of systemic disease except that she does not eat properly. She also complains of loss of appetite only. She also told that all her blood reports are normal which were done one month back. On examination, all nails of fingers and toes are flat and appear to adherent to nail beds.

Diagnosis:

Flat nails of fingers and toes

Treatment and Advice:

Patient is given Composition B to apply locally twice a day and advised to keep nails moisturized. Patient is directed to revisit after 20 days.

Patient $2^{nd}$ Visit:

Patient Revisited 20 days after the first visit. Her mother states that her nails are somewhat raised to nail beds. On examination of patient nails of hand and feet, appears to slightly rise. Patient is advised to revisit after one month.

Patient $3^{rd}$ Visit:

Patient revisited one month after the previous date. Mother says that nails are improving and rising from the nail bed. On examination nails are raised. Patient is given now again Composition B and advised to revisit after one month.

Patient 4th Visit:

Patient visited one month after the previous date. Her mother seem to be very happy and states that all of her nails with the exception of two nails has become completely normal with raised to nail bed and have acquired convexity and luster also. Now patient is given Composition A for maintenance and advised to apply furthermore and revisit after one month.

Patient $5^{th}$ Visit:

Patient visited one month after the previous visit and says that her all nails have become normal now with convexity. On examination of patient nails, nail had become normal. Drug is stopped and advised to patient keep her nails moisturized Patient $6^{th}$ Visit:

Patient visited one year after the previous date with complete cure and no reoccurrence of diseased.

Patient: F

Age: 40
Gender: Male
Status: Married, high socioeconomic, Engineer
History of Complaints of Patient:

Patient complains of deformed, roughness with strie nail for the last one year. He says that his all nails were normal one year back while he felt to develop roughness and strie in his index fingers of left nail in spite of getting different treatment, it was not going to be improved. He also says his rest of nails are normal.

On Examination of Patients:

On examination of patient, all of his nails of fingers and toes are of normal texture except roughness deformed and strie in left index fingers. Patient does not give history of any skin disease. I examined whole of his skin, he has no skin lesions at any spot. Patient gives the history of Diabetes Mellitus for the last 3 years. Except Diabetes Mellitus, he has no other systemic disease Diagnosis:

Deformed Rough strie nail.

Treatment and Advice:

Patients is given Composition A and advised to apply locally twice a day and visit after one month.

Patient $2^{nd}$ Visit:

Patient visited one month after the previous visit and said that he has got improvement; the nail growing from proximal is being corrected. He also says that nail growth is also increased. He is cutting nail and the nail from growing place emerging normal. On examination, there is marked improvement. Patient is given same Composition A and to apply in same way and advised to revisit after one month.

Patient $3^{rd}$ Visit:

Patient visited one month after the previous visit with remarkable improvement ad was very happy to say now his deformed nail of index fingers has adapted normal texture. On examination his nail is growing from proximal is adapting normal texture declining of lining and deformity. Composition A is given to apply locally and advised to revisit after one month.

Patient 4th Visit:

Patient revisited one month after the previous visit with highly remarkably improvement. Nails proximally growing are attending normal texture and declining lining stria and deformity. Patient is given same Composition A and is advised to revisit after one month.

Patient: G

Age: 18
Gender: Female
Status: Unmarried, Student and Low Socio Economic.
History of Complaints of Patient:

Patient states that her nails were with normal growth and structure while she felt splitting of her fingers nails in her two fingers, while the small pieces may flake and the nails grow and flake at the tip of the fingers which gradually developed to split and flake in whole nails fingers of hands.
On Examination of Patients:

On examination of the patient her whole fingers nails of hands were split into pieces and the growth of nails were restricted till tip of the fingers. On examination of the nails, nails are lusterless also further examination of her skin there is no any indication of skin disease. She says that her hands remain mostly in water. She is not giving any history of current or previous systemic or any skin diseases.
Diagnosis:

Splitting of nails into layers (onychoschizia) (Lamiler Dystrophy)
Treatment and Advice:

Patient is given Composition B and advised to apply locally twice a day and revisit after 20 days. Patient is also advised to remain away from water and also keeps her nails moisturized.
Patient $2^{nd}$ Visit:

Patient visited 20 days after previous visit and says that her nails are improving and now the splitting of nails is declined up to an extent. Patient is given same Remedy B and advised to apply in same way as previously and revisit after one month.
Patient $3^{rd}$ Visit:

Patient visited one month after previous visit and is very happy as she says that her splitting of nails has been subsided to a great extent and her nails are growing without splitting now beyond the tips of fingers. Now she is given Remedy A and advised to apply the medicine locally as previously and revisit after one month.
Patient 4th Visit:

Patient visited one month after the previous visit and says that now her nails are 90% improved and very less splitting than before. On Examination of her nails there appears to be not any deformity. Patient is given the remedy A for maintenance and advised to revisit after one month.
Patient $5^{th}$ Visit:

Patient visited one month after the previous visit and says that now she has got 100% cure and there is no splitting of nails. On examination her nails appears to be normal the treatment is stopped and advised the patient if she feels any problem she can come back or normally revisit after 6 month.

Patient: H

Age: 52
Gender: Male
Status: Married, Labor, Poor Socio Economic
History or Complaints of Patient:

Patient complains of his brittle nails since last 6 months in his all nails of hands and feet fingers. He also complains of lusterless and dry nails. Patient says that his nails are brittle and breaking since 6 months.
On Examination of Patients:

On examination of patient, his nails are brittle and lusterless. His all fingers and toes nails are affected. On examination of his skin there is no any lesion on skin. Even patient doesn't give any current or previous history of skin or any systemic diseases except that 8 months back he had iron deficiency anemia for which he had got treatment and his anemic condition was improved. Patient says that after correction of his even anemic condition, he felt brittleness in his nails. Although his anemic condition is corrected but nails are still brittle.
Diagnosis:

Brittle of nails due to iron deficiency anemia.
Treatment and Advice:

Patient is given Composition A and advised to apply locally twice a day on affected nails. He is also advised to take diet properly and revisit after one month.
Patient $2^{nd}$ Visit:

Patient visited one month after previous visit and says that now his brittle nails are improving. His nails are growing rapidly and nails from proximal end are correcting. He is given same Composition A and advised to revisit after one month.
Patient $3^{rd}$ Visit:

Patient visited one month after the previous visit and says that his nails are improved more. He is given same Composition A to apply locally twice a day and advised to revisit after one month.
Patient 4th Visit:

Patient visited one month after the previous date and says that he is now improved up to an extent. Nails from proximal ends are adopting normally and are not brittle. Same Composition A is given and advised to revisit after one month.
Patient $5^{th}$ Visit:

Patient visited one month after the previous date and says that there is marked improvement. Nails are returning back to its previous condition but still somewhat brittle. Same Composition A is given and advised to revisit after one month.
Patient $6^{th}$ Visit:

Patient revisited one month after the previous visit with near about complete cure. His remedy is stop and advised to keep his diet balance also.

Patient: I

Age: 8 yrs.
Gender: Male
Status: Primary class student
History or Complaints of Patient:

Patient's mother complains of her child that his nails do not grow beyond the tip of fingers for the last one year. Mother states that his nails of both hand's fingers were normal two years back. But after that all fingers nails of both hands are not growing beyond the tip of fingers. Mother also says that his toes fingers nails are growing normally
On Examination of Patients:

On examination of all nails of toes and fingers, toes nails are normal but fingers nails of both hands growth are restricted at the tip of the fingers. On examination of hands fingers nails appears to be bitten and after asking the mother, She told that he was habitual of biting his fingers nails after that nails restricted to grow but even after leaving the biting of nails since last six months, even though nails are not growing normally. These restricted growths of nails are due to continuous biting of nails.

Diagnosis:
  Diminished nail growth due to biting.
Treatment and Advice:
  Patient is given Remedy B to apply locally on all fingers nails twice a day and advised to keep the nails moisturized. Patient is advised to revisit after one month.
Patient $2^{nd}$ Visit:
  Patient revisited one month after the previous visit. Mother states that his nails are now growing. Same Composition B is given to apply in same way as previously and revisit after one month.
Patient $3^{rd}$ Visit:
  Patient revisited one month after previous visit. Mother is very happy to say that nails have started to grow normally. On examination of nails of patients, nails are grown beyond the tip of the fingers. Patient is given now Composition A to apply in same manner as previously and advised to revisit after one month.
Patient 4th Visit:
  Patient visited one month after the previous visit. Mother is now very happy to say that now she is cutting the nails of his child and afterwards these nails are growing. Medicine is stopped and patient is advised to moisturize his nails. Patient is also advised not to apply any medicine and revisit just for checking after 6 months.
Patient $5^{th}$ Visit:
  Patient visited 6 months after the previous date for checkup. Mother is very happy to say that now his nails are growing properly and normally as these were before the disease.

Patient: J

Age: 72
Gender: Male
Status: Labor, Lowest socioeconomic, neglected
History or Complaints of Patient:
  Patient complains of his deformed nail of right foot big toe nail. He complains that he has come to you because of the deformed nail with raised from the nail bed and has acquired a strange shape. Patient also complains of severe pain if it is touched to any solid object. He also says that he does not remember the time period but it is since long time.
On Examination of Patients:
  On examination of the toe's nails of the patient, it resembles like RAM'S HORNS. Patient looks and attitude is appearing to be deficient in diet and is neglected person in the society. He is Labor and he says that no one does care of him in his family. He even does not cut his nails since long time. He also says that he had to face trauma in his nail so many times. His wife was died 8 years back and now days no one keeps care of him. On overall examination, his all nails are not in normal texture, some nails have got style and some are brittle but he came to me because his one toe nail is creating great problem for him as he gets severe pain in it whenever it is touched to anything. He does not give the history of any local or systemic diseases but by appearance appears to be deficient in diet. Patient gives the previous history of surgical removal of this nail but it reoccurred like same
Diagnosis:
  Onychogryphosis (Ram's Horn Nails)
Treatment and Advice:
  As there is no specific treatment of it but Some recommend avulsion of the nail plate with surgical destruction of the nail matrix with phenol or the carbon dioxide laser, if the blood supply is good. Even after getting treatment of surgical destruction, Patient again develop same Ram's Horn like nails within 3 months. I first adopted the Treatment to cut the $\frac{3}{4}^{th}$ nail which was raised from the nail bed and laid the rest of the nail remaining as it is. Then I gave the patient Composition B to apply locally from the remaining part of nail so that nail from the root might be growing normally and remain attached to nail beds. Patient is advised to keep the nails moisturized and revisit after one month.
Patient $2^{nd}$ Visit:
  Patient visited one month after the previous date to say that his growing nails are appearing to be coming with the attachment of nail bed. On examination of his disease nail, Nail appear to be somewhat growing normally proximally and still are raised from the bed but very little. Patient is given the same Composition B and advised to apply the drug in same way locally twice a day and revisit after one month.
Patient $3^{rd}$ Visit:
  Patient visited one month after previous visit to say it is improving. On examination, Nail growth was increased and the nail was attached to nail bed somewhat but not like previously raised. Patient is again given the same Composition B and advised to revisit after 2 months and keep the nails moisturized.
Patient 4th Visit:
  Patient visited 2 months after the previous date to say that now the nail have been improved to an extent and it is not raised from the nail bed too much. He is also not feeling pain. Patient is given again the same Composition B and advised to revisit after 3 months again.
Patient $5^{th}$ Visit:
  Patient visited 3 months after the previous visit with the complete eruption of new growth of nail and is very happy but says that still it is raised from the nail bed but not like previous one like Ram's horns and is improved and not feels pain even if it is touched with any of the object. Patient is given the same Composition Band advised to revisit after 3 month and advise to apply the drug locally in same way as previously.
Patient 6th Visit:
  Patient visited 3 months after the previous visit with quite happy and says that now his most of the proximal part of the nail have become normal and is attached to nail bed but distal part still raised from the nail bed but he does not feel any pain. On examination of hi affected nail, it has adopted normal texture up to a great extent and the half of the nail are attached with the nail bed and the distal part of nail is still raised from the nail bed but not to that extent as it was previously. Nail from the proximal part is getting normal texture. Patient is cutting his nail as it grows beyond the tip of the finger. Patient is given now Composition A to apply locally as previously and maintenance dose and advised to apply it regularly for two to four months more and revisit afterwards.
Patient 7th Visit:
  After the last visit, Patient did not come back.
  The active compositions of this invention are rapidly and highly soluble in water and thus are rapidly absorbed onto and into nails, wet skin rather than on dry skin. It is thus preferred that the compositions be topically applied to skin/nail surface that has been moistened with water.
  As the active composition when applied to the skin can create dryness, it is thus desirable to have a formulated pharmacological composition that is greasy. However, when treating acne this drying ability is beneficial and thus the final composition should be non-greasy or have less of a greasy feel or property.

The active compositions are rapidly absorbed per cutaneously and enter in to the bloodstream. Therefore it is advisable that when the drug is applied to a large area, for example in the treatment of psoriasis, the patient should be kept under observation by the physician.

The active composition may also lower blood pressure as it is absorbed through the skin. It is thus advisable not to treat patients less than 5 years old or applied under strict supervision at a low concentration of active composition and/or treating small areas.

If given orally it may cause nausea, vomiting and diarrhea. It therefore should be taken a half hour before food or one hour after food.

While various changes may be made in the detailed construction and processes of this invention, it will be understood that such changes will be within the spirit and scope of the present invention. Having thus described the invention in detail, it is to be understood that the foregoing description is not intended to limit the spirit and scope thereof. What is desired to be protected by Letters Patent is set forth in the appended claims.

What is claimed:

1. A method of treating a deformed nail in a patient having a deformed nail, comprising:
   topically applying to the deformed nail a therapeutically effective amount of a pharmacological composition comprising:
   a pharmaceutical carrier;
   an active composition consisting of an amount of about 2% to 10% a mixture of sodium oxalate and oxalic acid;
   wherein the pharmacological composition is safe and effective for the treatment of the deformed nail.

2. The method of claim 1, wherein the mixture of sodium oxalate and oxalic acid is about 73% to about 83% sodium oxalate and about 17% to about 27% oxalic acid.

3. The method of claim 1, wherein the mixture of sodium oxalate and oxalic acid is about 78.44% of Sodium oxalate and about 21.56% oxalic acid.

4. The method of claim 1, wherein the pharmacological composition additionally includes about 1% by weight of hydrocortisone.

5. The method of claim 1, wherein the pharmaceutical carrier is a composition consisting of an oil and water emulsification.

6. The method of claim 1, wherein the pharmacological composition consists of about 5% of the active composition.

7. The method of claim 1, wherein the pharmacological composition is applied at least twice a day.

* * * * *